US00PP35015P2

(12) United States Plant Patent
Lyrene et al.

(10) Patent No.: US PP35,015 P2
(45) Date of Patent: Mar. 7, 2023

(54) BLUEBERRY PLANT NAMED 'FL09-216'

(50) Latin Name: ***Vaccinium corymbosum* L.**
Varietal Denomination: FL09-216

(71) Applicant: Florida Foundation Seed Producers, Inc., Marianna, FL (US)

(72) Inventors: Paul M. Lyrene, Micanopy, FL (US); James W. Olmstead, Aptos, CA (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/576,179

(22) Filed: Jan. 14, 2022

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

PP12,165 P2 10/2001 Lyrene
PP20,695 P2 2/2010 Wright et al.

OTHER PUBLICATIONS

Garden Media Group (Year: 2021).*
U.S. Appl. No. 17/576,191, filed Jan. 14, 2022, Lyrene et al.

* cited by examiner

*Primary Examiner* — Keith O. Robinson
(74) *Attorney, Agent, or Firm* — Dentons US LLP

(57) ABSTRACT

'FL09-216' is a new and distinct southern highbush blueberry (*Vaccinium corymbosum* L.) variety distinguished at least by a low chilling requirement, vigorous, bushy growth habit, high early yield, good field disease resistance, and large fruit that are sweet and exhibit small, dry picking scars.

7 Drawing Sheets

Latin name of the genus and species of the plant claimed: *Vaccinium corymbosum* L.

Variety denomination: 'FL09-216'.

BACKGROUND OF THE INVENTION

The invention relates to a new and distinct hybrid variety of southern highbush blueberry (*Vaccinium corymbosum* L.) plant named 'FL09-216'. 'FL09-216' originated as a seedling that was generated from a cross performed in Gainesville, Fla. during February of 2006 between 'FL01-06' (unpatented), as the female (seed) parent, and 'C99-42' (Kirra) (U.S. Plant Pat. No. 20,695), as the male (pollen). The seedling was planted in a high-density field nursery in May of 2007, and the first fruit were evaluated in April of 2008. After the second year of fruiting in the original field, 'FL09-216' was propagated by softwood stem cuttings during the spring of 2009. The softwood stem cuttings were rooted in Gainesville, Fla. during summer 2009. 'FL09-216' was established in a pre-commercial field experiment with 15-plant test plot during winter of 2010 for a variety test in Windsor, Fla. It was during this variety test that the experimental code 'FL09-216' was assigned. Based on the growth, yield and fruit quality of this plot, 'FL09-216' was repropagated by softwood stem cuttings and additional experimental test plots ranging from 5 to 45 plants were established for experimental research trials throughout Florida in 2014. These plots have been observed during flowering and ripening each year since establishment, and no mutations or off-type plants have been observed.

SUMMARY OF THE INVENTION

'FL09-216' differs from its parents and all other known southern highbush blueberry plants. The following are the most distinguishing characteristics of 'FL09-216' when grown under normal horticultural practices in Florida: (1) a very low chilling requirement, particularly for the flower buds; (2) a vigorous, bushy growth habit; (3) earlier ripening (from mid-late March through mid-May, when grown as a deciduous plant in north central Florida); (4) very high tendency to evergreen; and (5) large, firm, berries that exhibit small, dry picking scars.

'FL09-216' plants can be readily and unambiguously distinguished from those of its parents at least based upon its bushy plant architecture. This is because 'C99-42' has a spreading growth habit. The early fruit yield exhibited by plants of 'FL09-216' is significantly earlier and higher than that of either parent.

Blueberry variety 'Emerald' (U.S. Plant Pat. No. 12,165) is planted throughout the southeastern United States. 'FL09-216' is believed to be most similar to 'Emerald'. Nonetheless, 'FL09-216' and 'Emerald' can be readily and unambiguously distinguished at least based upon growth habit, the time at which their fruit is produced, and the fruit cluster tightness. Plants of 'FL09-216' display a bushier habit and are smaller in size compared to 'Emerald'. Plants of 'FL09-216' produce their fruit significantly earlier than those of 'Emerald' when no growth regulator is used, and the fruit cluster of 'Fl09-216' are lose compared to the tight cluster of 'Emerald' . 'FL09-216' is not similar to its parents or 'Emerald' particularly because of its growth habit (bushy-small).

BRIEF DESCRIPTION OF THE DRAWINGS

'FL09-216' is illustrated in the accompanying photographs of 6-year old specimens, which show the plant's flowers, fruit, leaves, and form. Colors shown are as true as can be reasonably reproduced by photographic procedures and may differ from those cited in the detailed description, which accurately describe the colors of 'FL09-216'.

DETAILED BOTANICAL DESCRIPTION

Figure 1:
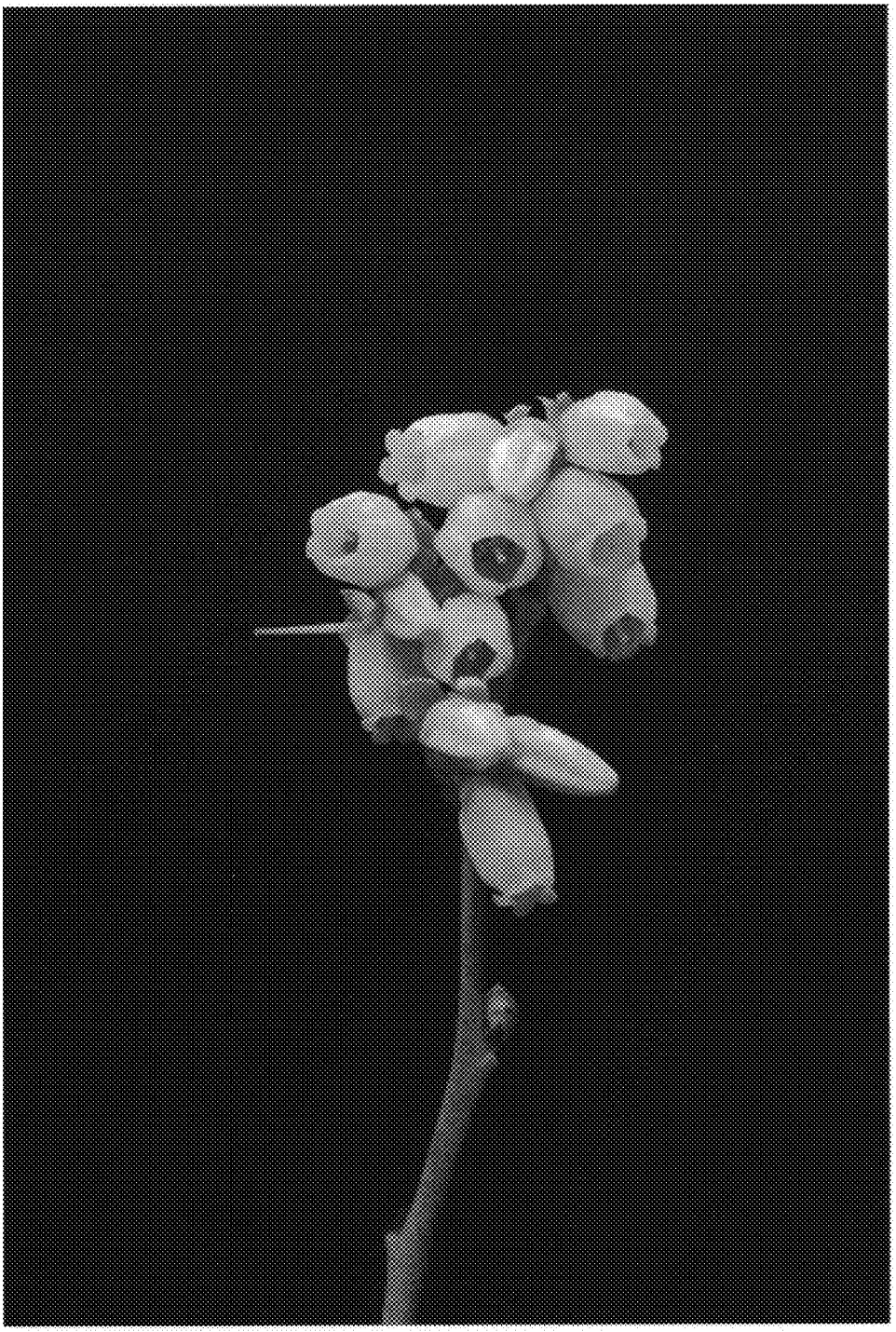
FIG. 1—Shows clusters of opening 'FL09-216' flowers on the branch.
Figure 2:
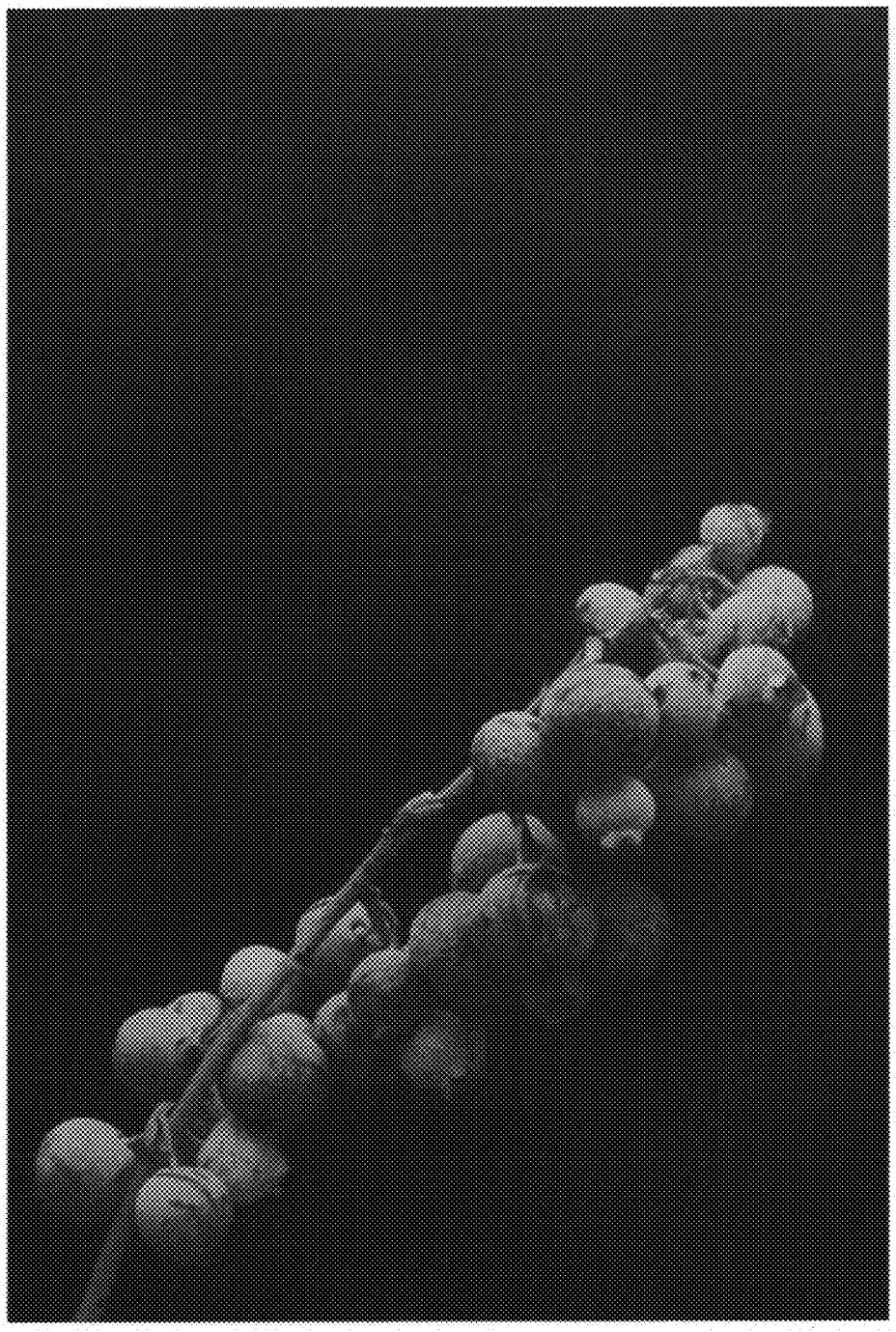
FIG. 2—Shows clusters of 'FL09-216' berry fruits on the branch.
Figure 3:
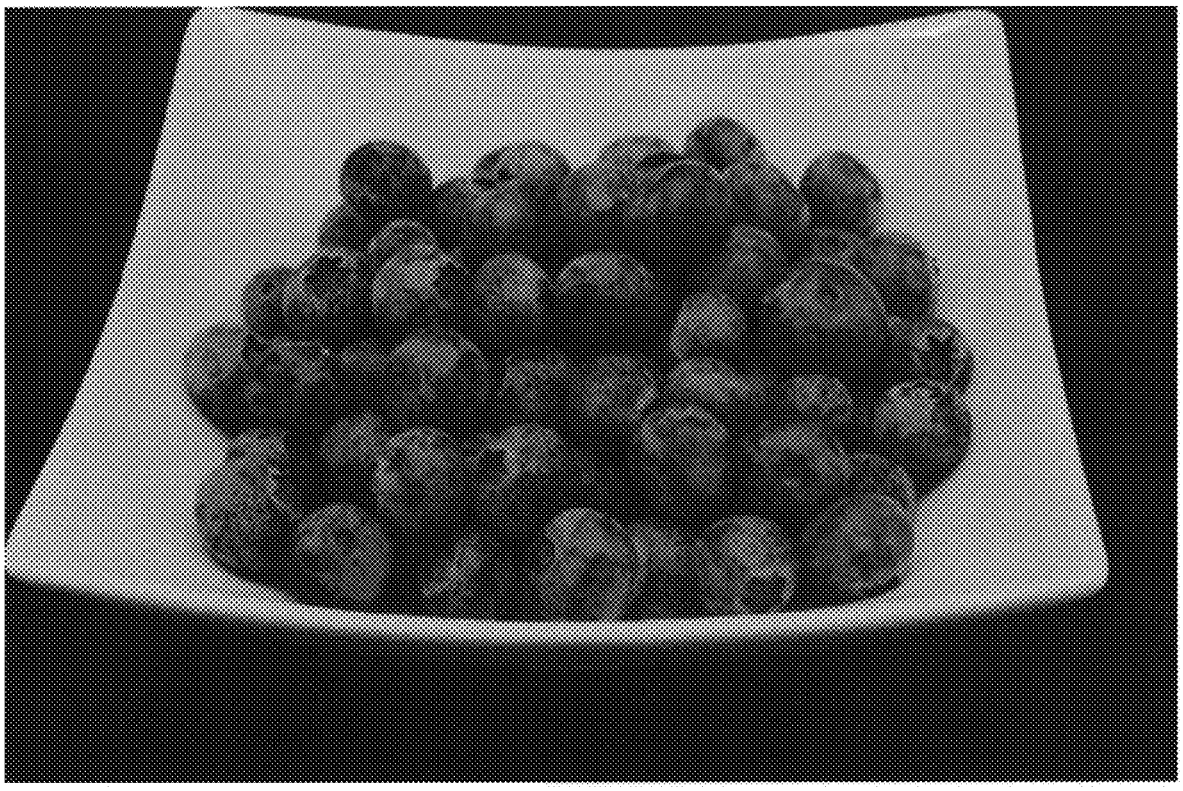
FIG. 3—Shows a close-up of harvested 'FL09-216' berries.
Figure 4:
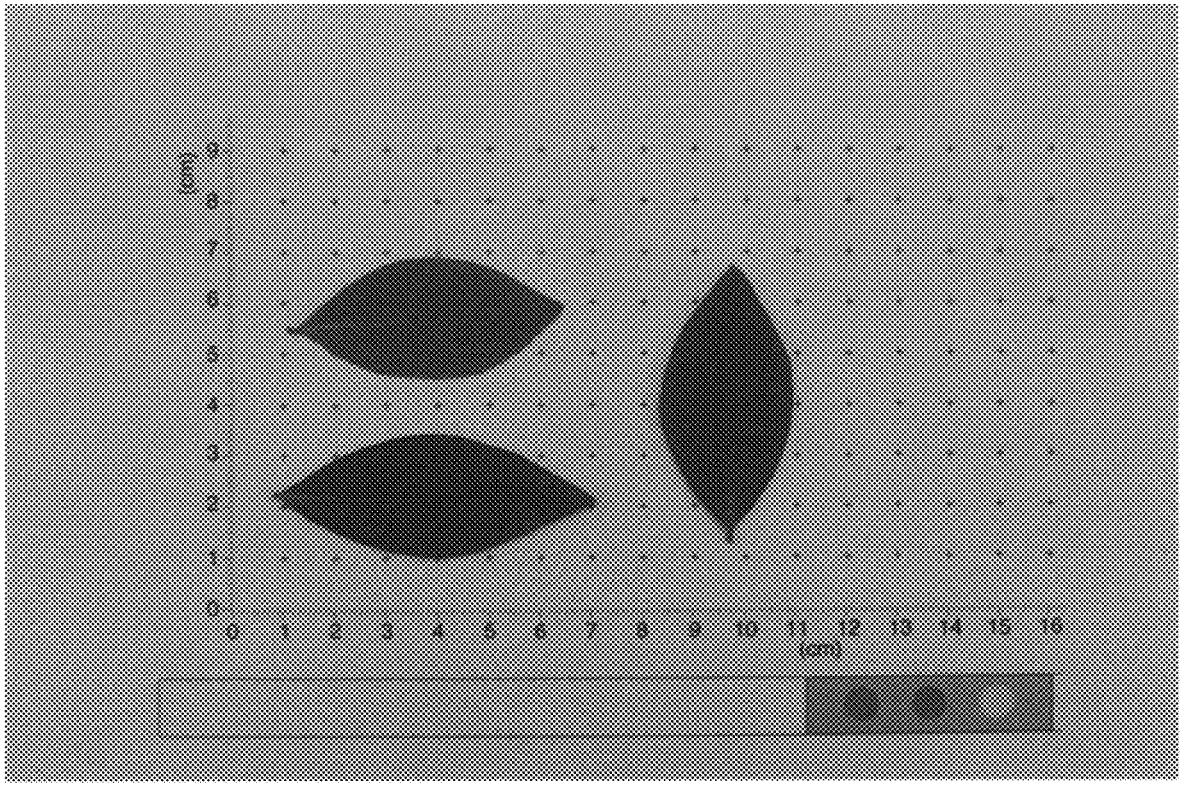
FIG. 4—Shows a close-up of mature 'FL09-216' leaves with a scale bar.
Figure 5:
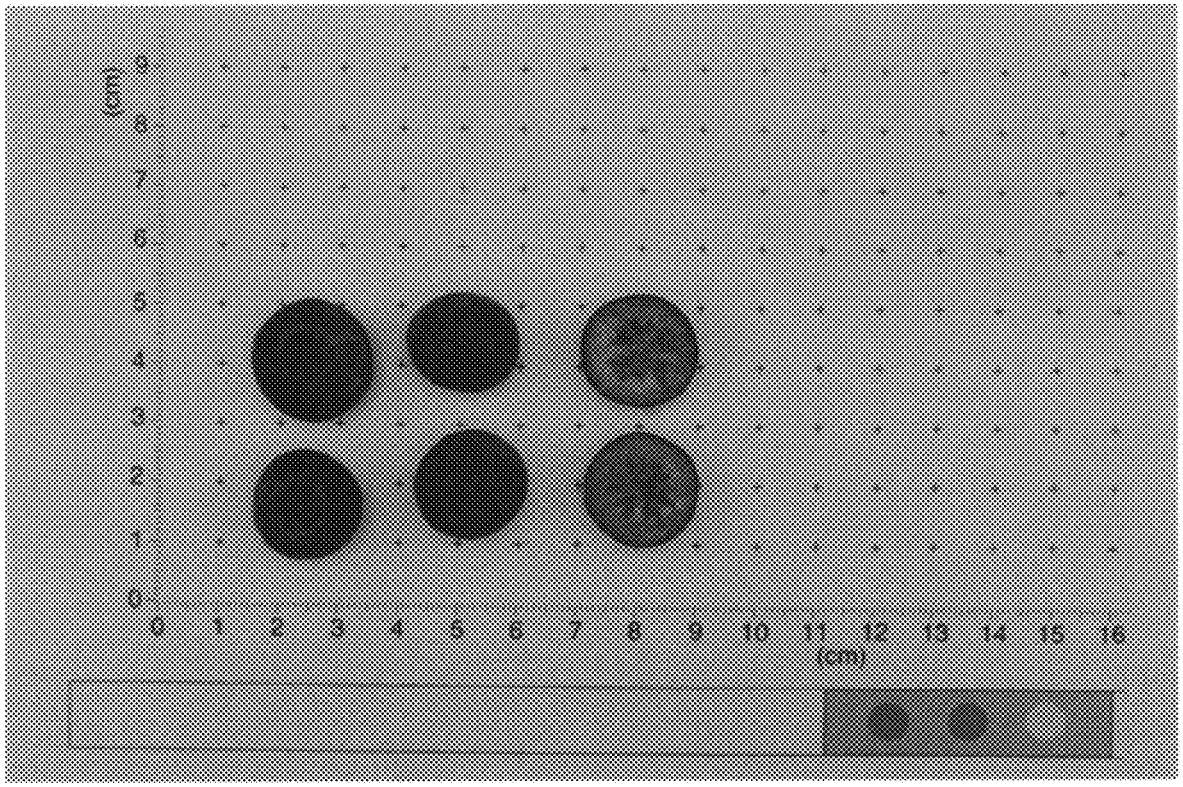
FIG. 5—Shows a close-up of mature 'FL09-216' fruit with a scale bar.
Figure 6:
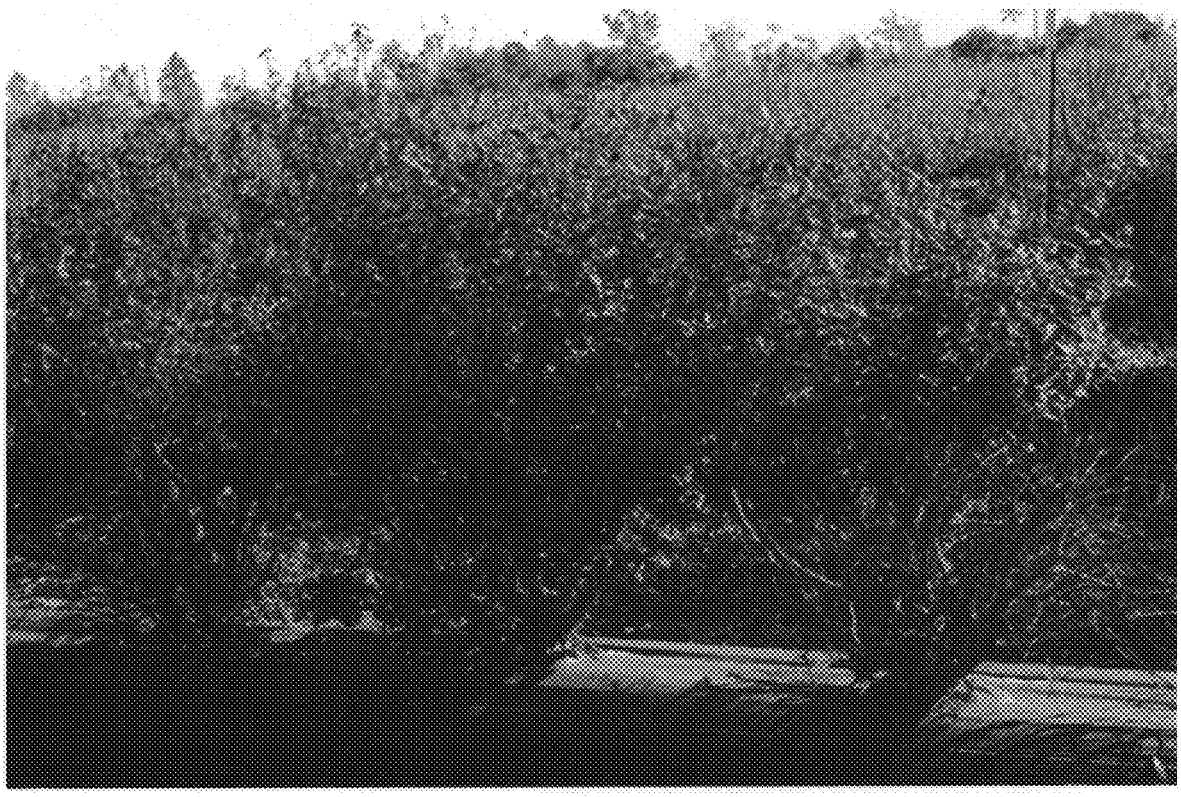
FIG. 6—Shows 6-year-old 'FL09-216' plants during the winter
Figure 7:
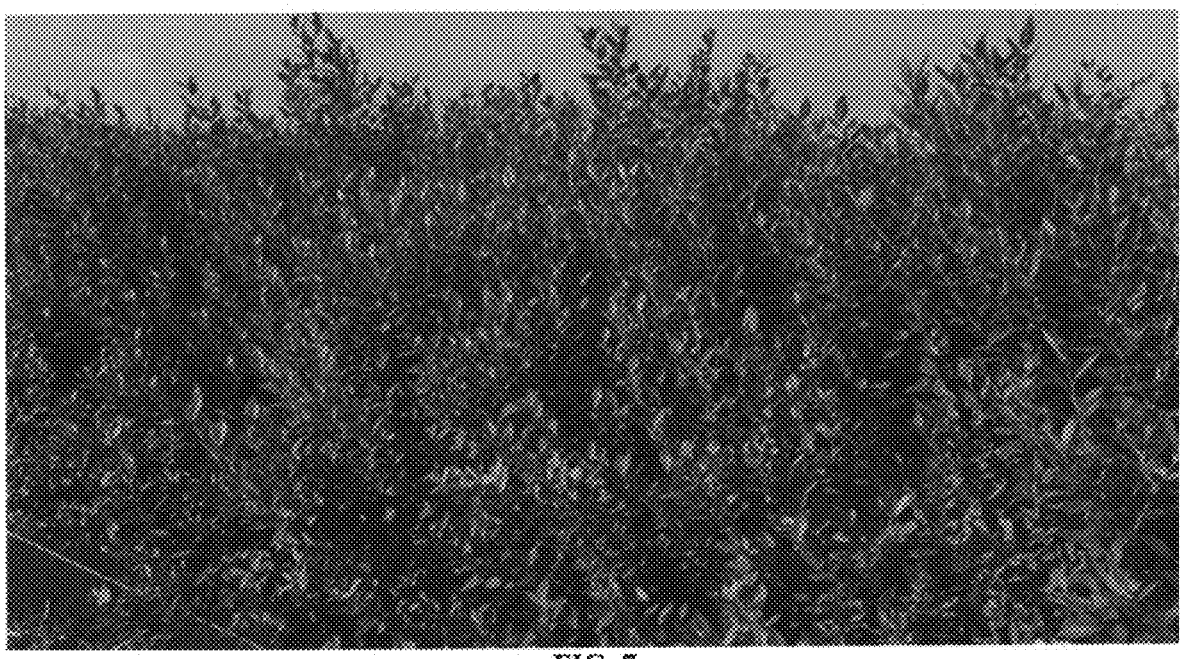
FIG. 7—Shows 5-year-old 'FL09-216' plants during the summer

The following detailed description sets forth distinctive characteristics of 'FL09-216'. The data that define these characteristics were collected from asexual reproductions carried out in Florida. The plant history was taken on a plot of plants growing in an experimental trial near Waldo, Fla. (2014 research block stg.4 plots). The plants were 6 years of age when the data was collected. Certain characteristics may vary with plant age. 'FL09-216' has not been observed under all possible environmental conditions, and the measurements given may vary when grown in different environments. Color descriptions are based on The Royal Horticultural Society (R.H.S.) Colour Chart by the Royal Horticultural Society, London, 6th Edition, (2015). If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'FL09-216'.

Plant:

*Plant vigor*.—High.

*Growth habit*.—Bushy to Semi-bushy, Round bush architecture.

*Plant height*.—1.34 m on average for 6-year old plant.

*Plant spread*.—1.68 m on average for 6-year old plant.

*Flower bud density* (*number*) *along flowering twigs in January*.—Medium.

*Twigginess*.—Moderate.

*Tendency toward evergreen-ness*.—Low.

*Productivity*.—In northeast Florida, 'FL09-216' produces 5.75 kg per season from plants 5 years old or older when hand harvested.

*Chilling requirement*.—50-100 hours below 7° C.

*Cold hardiness*.—'FL09-216' has been grown in temperate climates with extremely cold winter temperatures. Plants have survived winter freezes of −7° C. with minimal damage.

*Ease of propagation*.—'FL09-216' has only been propagated from softwood stem cuttings, where the rooting percentage is greater than 85% and comparable to other varieties.

Trunk and branches:

*Suckering tendency*.—Medium.

*Surface texture*.—Strong 12-month-old shoots (observed in October): Smooth with some presence of pubescence (little to no presence of ridges and bark-like structure). Surface texture (of 3-year-old and older wood): Rough with presence of bark-like structures

*Color*.—Color of new twigs observed in the field: Fan 3 Yellow-Green Group 144 Strong Yellow Green C. Color of 3-year-old, rough-textured canes: Fan 4 Brown Group N200 Light Grey D with some hints behind bark of Fan 4 Greyed-Orange Group N167 Brownish Orange A.

*Internode length average* (*strong, upright shoots measured in June*).—10.8 mm.

Leaves:

*Leaf arrangement*.—Alternate, Fibonacci Spiral.

*Length* (*including petiole, from tip of petiole to end of blade*).—Average of 5.17 cm.

*Width* (*at widest point*).—Average of 2.43 cm.

*Petiole length*.—Average of 2.95 mm.

*Petiole diameter*.—Average of 1.73 mm.

*Leaf shape*.—Elliptic-partially lanceolate.

*Leaf base shape*.—Elliptic

*Leaf venation pattern*.—Cross-Venulate.

*Margin*.—Entire.

*Color*.—Upper surface: Fan 3 Green Group 137 moderate Olive-Green G. Lower surface: Fan 3 Green Group 147 moderate Yellow-Green C. Leaf Vein Color: Fan 3 Yellow -Green Group 145 Light Yellow Green C. Leaf petiole color: Fan 3 Yellow-Green Group 144 Strong Yellow Green C.

*Pubescence*.—Upper surface of leaves: Absent. Lower surface of leaves: Absent. Margins: Some presence.

*Timing of vegetative bud burst* (*early, medium, late*).—Early.

*Relative time of leafing versus flowering*.—When not treated with hydrogen cyanamide in mid-winter, leafing occurs during flowering.

Flowers:

*Arrangement*.—Flowers are arranged alternately along short branches with leaves.

*Fragrance*.—Very slight floral fragrance.

*Shape*.—Urceolate and cylindrical.

*Flowering period*.—50% anthesis was observed Feb. 1, 2021 Waldo, Fla. in Stage IV 2014 block (6 yr old plants).

*Cluster*.—Medium.

*Number of flowers per cluster*.—Mean of 4.5.

*Pedicel*.—Length at time of anthesis: Average of 3.97 mm. Color at time of anthesis (non sun exposed side): Fan 3 yellow-green group N144 Strong Yellow green C with hints of Fan 2 red-purple group 61 deep-purplish red A on the sun exposed side.

*Peduncle*.—Length at time of anthesis: Highly, variable, average of 11.43 mm. Color at time of anthesis (non sun exposed side): Fan 3 yellow-green group N144 Strong yellow green C with Hints of Fan 2 red-purple group 61 Deep purplish Red A on sun exposed side.

*Calyx*.—Surface texture: Smooth with slight wax. Diameter: Mean of 4.6 mm. Color (outer surface, visible at the time of anthesis without removing the corolla tube): Fan 3 green group 137 moderate olive green B with Fan 3 green group 138 moderate yellow green B on tips of calyx lobes.

*Corolla*.—Diameter: mean of 5.73 mm. Length (from pedicel attachment point to corolla tip excluding the pedicel): Mean of 10.49 mm. Aperture diameter: Mean of 2.49 mm. Texture: Smooth. Color: Fan 4 greyed-white group 156 yellowish white D. Anthocyanin coloration in tube: Absent.

Reproductive organs:

*Style*.—Length (top of ovary to stigma tip): Mean of 7.83 mm. Color: Fan 3 yellow-green group N144 Strong Yellowish Green A. Location of tip of stigma relative to tip of the corolla: 0.73 mm.

*Anthers*.—Color: Fan 4 greyed-orange group N170 Brownish Orange A. Pollen: High. Pollen germination: Typically, greater 90%. Color: Fan 4 Yellow-Green Group N144 Strong Yellow Green D. Filament length: 6.41 mm. Filament width: 1.07 mm.

*Self-fruitfulness*.—Low to medium. Planting in the field configurations that promote cross fertilization with other southern highbush varieties is recommended for all southern highbush blueberry plants grown in Florida.

Fruit:

*Mean date of* 50% *harvest in Citra, Fla*.—Between weeks $15^{th}$ and $16^{th}$.

*Diameter of calyx aperture on mature berry*.—Mean of 6.5 mm.

*Size and shape of calyx lobes on mature berry*.—Small to medium, erect to incurving, with a dry shallow calyx basin.

*Pedicel length on ripe berry*.—Average of 6.26 mm.

*Detachment force for ripe berries* (*easy, medium, hard*).—Easy.

*Fruit cluster density* (*sparse, medium, dense*).—medium.

*Number of berries per cluster*.—Average of 3.16

*Fruiting type*.—On one-year-old shoots and current season's shoots.

Berry:

*Cluster* (*tight, medium, loose*).—Medium.

*Weight* (*on well-pruned plants*).—Average of 1.84 g.

*Height*.—Average of 12.77 mm.

*Width*.—Average of 15.89 mm.

*Shape*.—Round slight oblate

*Surface color of mature berries ripe on the plant*.—Fan 2 violet-blue group 97 Light Purplish Blue B.

*Intensity of fruit bloom*.—High.

*Surface color of ripe berry after polishing*.—Fan 4 Black Group 202 Dark greyish Purple A.

*Immature berry color, with bloom*.—Fan 3 Green group 140 light Yellowish green D.

*Immature berry color, without bloom*.—Fan 3 Green Group 142 Brilliant yellow green B.

*Flesh color*.—Fan 3 Yellow green group 145 light yellow green D.

*Surface wax*.—Medium and moderate persistence.

*Pedicel scar*.—Small and dry. Average of 1.67 mm.

*Firmness*.—Very firm, average 249.13 g/mm.

*Flavor*.—Moderate sweetness, mild acidity.

*Intensity of fruit sweetness*.—Medium.

*Texture*.—Good non-mealy, fleshy texture and no stone cells present.

*Fruit storage quality*.—Fruit is firm and can be stored without shriveling, mold or loss of firmness for 3 weeks at 4° C.

Seeds:

*Color of dried seeds*.—Fan 4 Greyed Orange Group N167 Brownish Orange A.

*Weight of well-developed dried seeds*.—Average of 14 0.56 mg.

*Length of well-developed dried seeds*.—Average of 1.98 mm.

*Width of well-developed dried seeds*.—Average of 1.17 mm.

Use: Produces southern highbush blueberries suitable for hand harvest for the fresh fruit markets.

Resistance to diseases, insects, and mites: 'FL09-216' has grown vigorously and shows good bush survival in the field, with very low number of plants dying soon after planting. Reaction to the various fungal species that cause summer leaf spots (including rust) is lower than those of other southern highbush varieties. Appears to be more susceptible than other cultivars to stem blight (*Botryosphaeria*). Fungicide applications may be needed after harvest to reduce foliar and stem diseases and retain leaves into the fall for maximum flower bud set. Appears to be more tolerant than other southern highbush varieties to spider mites. Susceptibility to typical blueberry insect and mite pathogens such as spotted wing *Drosophila* (*Drosophila suzukii*), blueberry gall midge (*Dasineura oxycoccana*), blueberry flower thrips (*Frankliniella* spp), and blueberry bud mite (*Acalitus vaccini*) appear similar to other southern highbush.

What is claimed is:

1. A new and distinct variety of southern highbush blueberry plant named 'FL09-216' as shown and described herein.

* * * * *